_(12)_ United States Patent
Kagiya et al.

(10) Patent No.: US 7,462,601 B2
(45) Date of Patent: Dec. 9, 2008

(54) AMELIORANT FOR CHEMICAL TREATMENT OF CANCER

(75) Inventors: Tsutomu Kagiya, 3-16, Yoshidakaguraokacho, Sakyo-ku, Kyoto-shi, Kyoto 606-8311 (JP); Hironobu Murase, Gifu (JP); Nina Petrovna Konovalova, Moscow (RU); Ludmila Mihailovna Volkova, Moscow (RU); Nataliya Yurievna Lugovskaya, Moscow (RU); Lubov Sergeevna Vasilieva, Moscow (RU)

(73) Assignee: Tsutomu Kagiya, Kyoto (JP)

( * ) Notice: Subject to any disclaimer, the term of this patent is extended or adjusted under 35 U.S.C. 154(b) by 224 days.

(21) Appl. No.: 10/507,760

(22) PCT Filed: Mar. 26, 2002

(86) PCT No.: PCT/JP02/02914

§ 371 (c)(1), (2), (4) Date: Sep. 15, 2004

(87) PCT Pub. No.: WO03/080075

PCT Pub. Date: Oct. 2, 2003

(65) Prior Publication Data

US 2005/0215492 A1 Sep. 29, 2005

(51) Int. Cl.
*A61K 31/70* (2006.01)
(52) U.S. Cl. ........................................... 514/34
(58) Field of Classification Search .................... 514/25, 514/27, 32, 33, 34; 536/4.1, 18.1
See application file for complete search history.

(56) References Cited

U.S. PATENT DOCUMENTS

| | | | | |
|---|---|---|---|---|
| 5,004,758 | A * | 4/1991 | Boehm et al. | 514/283 |
| 6,174,864 | B1 * | 1/2001 | Yoshikawa et al. | 514/28 |
| 7,071,158 | B2 * | 7/2006 | Chinery et al. | 514/1 |

FOREIGN PATENT DOCUMENTS

| | | |
|---|---|---|
| EP | 0 611 152 | 2/1994 |
| EP | 0 775 488 A1 | 11/1996 |
| EP | 0 775 488 | 5/1997 |
| EP | 0 819 433 | 1/1998 |
| JP | 09-249688 | 9/1997 |
| JP | 10 072356 A | 3/1998 |
| JP | 11-021291 | 1/1999 |
| JP | 11-035599 | 2/1999 |
| JP | 2001261563 A * | 9/2001 |

OTHER PUBLICATIONS

Igaku-No-Ayumi (Progress of Medical Science), 1993, vol. 164, No. 5, pp. 376-379.
European Search Report for Application No. EP 02 70 7164 dated Jan. 15, 2008.

* cited by examiner

*Primary Examiner*—Elli Peselev
(74) *Attorney, Agent, or Firm*—Mathews, Shepherd, McKay & Bruneau, P.A.

(57) ABSTRACT

An ameliorating agent for cancer chemotherapy is disclosed, which comprises a chromanol glycoside represented by the following general formula (1)

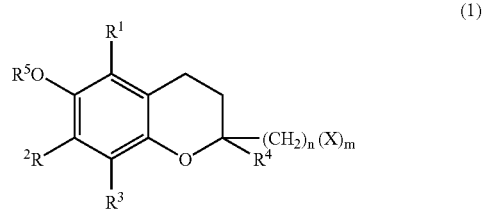

(wherein $R^1$, $R^2$, $R^3$, and $R^4$, which are identical or different from each other, stand for a hydrogen atom or a lower alkyl group, $R^5$ stands for a hydrogen atom, a lower alkyl group, or a lower acyl group, X stands for a monosaccharide residue or an oligosaccharide residue optionally having the hydrogen atom of the hydroxyl group in the saccharide residue substituted with a lower alkyl group or a lower acyl group, n is an integer in the range of 0-6, and m is an integer in the range of 1-6).

According to this invention, a novel ameliorating agent for cancer chemotherapy is provided which acts safely and effectively in a small dosage to enhance the carcinostatic action of an anti-cancer agent in cancer chemotherapy and repressing side effects by cancer chemotherapy as well.

2 Claims, No Drawings

AMELIORANT FOR CHEMICAL TREATMENT OF CANCER

TECHNICAL FIELD

This invention relates to a novel ameliorating agent for cancer chemotherapy. More particularly, this invention relates to an ameliorating agent for cancer chemotherapy containing as an active ingredient a water-soluble chromanol glycoside.

BACKGROUND ART

Cancers have been a disease that occupies the first position in the list of causes of death of the Japanese since 1981 and the number of patients of this disease has been increasing thence year after year. The basic research and clinical research regarding the therapy of cancer has been advancing on the global level over these 10-odd years. This development in association with the advance of the diagnosis of cancer has been making it feasible to ensure early detection and treatment of a cancer.

The therapy of cancer is based on a surgical operation, a radiotherapy, and a cancer chemotherapy (therapy using an anti-cancer agent). The cancer chemotherapy is a method for treating malignant neoplasm by the administration of an anti-cancer agent. Since an anti-cancer agent has no substantially different effects between cancer cells and normal cells, side effects thereof become severe in accordance with the improvement of treatment effects. Cisplatin, for example, has serious side effects such as renal dysfunction, nausea, vomiting, neuropathy, myelopathy like leukopenia, thrombocytopenia, and anaemia. The manifestation of such side effects which are caused by the cancer chemotherapy often entail such a situation as limiting the dosage of an anti-cancer agent and discontinuing the therapy. Further, the restraint of the side effects has an important influence on the life lengthening of a patient under treatment. In the execution of the cancer chemotherapy, therefore, it is a very important task to decrease the side effects without repressing the effects on the treatment with an anti-cancer agent.

As medicines for decreasing the side effects by the therapy with an anti-cancer agent, such 5-$HT_3$ acceptor antagonists as granisetron and ondansetron which are effective for nausea and vomiting and such bone marrow function activators as filgrastim and lenograstim which are effective for leukopenia have been known. In the field of cancer chemotherapy, the desirability for developing a novel ameliorating agent for cancer chemotherapy which enhances the carcinostatic action of an anti-cancer agent and represses various side effects thereof has been still finding popular recognition.

The chromanol glycoside which is used in this invention is a known compound (JP-A-7(1995)-118287, JP-A-9(1997)-249688, and JP-A-11(1999)-21291). The chromanol glycoside results from substituting an alcohol for the phytyl group at the 2 position of a chroman ring of a representative example of Vitamin E, α-tocopherol, and further linking saccharide thereto and has high water-solubility and excellent antioxidizing ability. The use of this chromanol glycoside as an ameliorating agent for the cancer chemotherapy, however, has never been known heretofore.

This invention has been attained in consideration of the problems of the prior art as described above. It is an object of this invention to provide a novel ameliorating agent for cancer chemotherapy which effectively functions safely in a small amount and exhibits excellent ability of repressing various side effects entailed by the cancer chemotherapy.

Another object of this invention is to provide a novel ameliorating agent for cancer chemotherapy which enhances carcinostatic function of an anti-cancer agent in the cancer chemotherapy.

DISCLOSURE OF THE INVENTION

The present inventors, after repeating a diligent study in search of an agent for repressing side effects by cancer chemotherapy, have found that the chromanol glycoside mentioned above can not only enhance carcinostatic function of an anti-cancer agent but also repress truly effectively various side effects entailed by the cancer chemotherapy. This invention has been perfected as a result.

To be specific, this invention is to provide an ameliorating agent for cancer chemotherapy which comprises a chromanol glycoside represented by the following general formula (1)

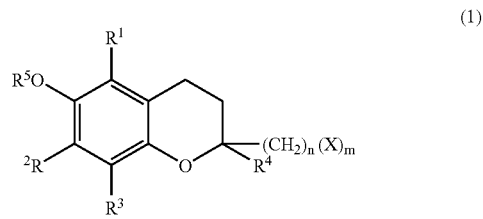

(wherein $R^1$, $R^2$, $R^3$, and $R^4$, which are identical or different from each other, stand for a hydrogen atom or a lower alkyl group, $R^5$ stands for a hydrogen atom, a lower alkyl group, or a lower acyl group, X stands for a monosaccharide residue or an oligosaccharide residue optionally having the hydrogen atom of the hydroxyl group in the saccharide residue substituted with a lower alkyl group or a lower acyl group, n is an integer in the range of 0-6, and m is an integer in the range of 1-6).

This invention also concerns an ameliorating agent for cancer chemotherapy mentioned above which is an agent for repressing side effects.

This invention also concerns an ameliorating agent for cancer chemotherapy mentioned above which is an agent for enhancing carcinostatic action.

This invention also concerns an ameliorating agent for cancer chemotherapy mentioned above, wherein the cancer chemotherapy is a therapy by the use of a cytotoxic anti-cancer agent.

This invention also concerns an ameliorating agent for cancer chemotherapy mentioned above, wherein the cytotoxic anti-cancer agent is an alkylating agent, an antineoplastic vegetable component-containing preparation, an antineoplastic antibiotic preparation, or a DNA chelating agent.

This invention also concerns an ameliorating agent for cancer chemotherapy mentioned above, wherein the cytotoxic anti-cancer agent is cisplatin, cyclophosphamide, or doxorubicin hydrochloride.

This invention also concerns an ameliorating agent for cancer chemotherapy mentioned above, wherein the chromanol glycoside mentioned above is 2-(α-D-glucopyranocyl)methyl-2,5,7,8-tetramethyl chroman-6-ol.

This invention also concerns an ameliorating agent for cancer chemotherapy which is a water-soluble preparation.

BEST MODE OF CARRYING OUT THE INVENTION

The ameliorating agent for cancer chemotherapy of this invention is characterized by having as an active ingredient thereof a chromanol glycoside represented by the aforementioned general formula (1).

In the general formula (1) mentioned above, the lower alkyl groups represented by $R^1$, $R^2$, $R^3$, $R^4$ and $R^5$ include suitably lower alkyl groups of 1-8, preferably 1-6, carbon atoms. As typical examples thereof, methyl group, ethyl group, propyl group, isoproplyl group, butyl group, isobutyl group, pentyl group, isopentyl group, hexyl group, heptyl group, and octyl group may be cited. Among these groups, methyl group or ethyl group proves particularly advantageous. The lower acyl groups represented by $R^5$ include suitably lower acyl groups of 1-8, preferably 1-6, carbon atoms. As typical examples thereof, formyl group, acetyl group, propionyl group, butyryl group, isobutyryl group, valeryl group, isovaleryl group, pivaloyl group, hexanoyl group, heptanoyl group, and octanoyl group may be cited. Among these lower acyl groups, acetyl group, propionyl group, or butyryl group proves particularly advantageous. As typical examples of the monosaccharide residue represented by "X", saccharide residues such as of glucose, galactose, fucose, xylose, mannose, rhamnose, fructose, arabinose, lyxose, ribose, allose, altrose, idose, talose, deoxyribose, 2-deoxyribose, quinovose, and abequose may be cited. The oligosaccharide residue represented by "X" includes residues of oligosaccharide having two to four monosaccharides as mentioned above combined such as, for example, maltose, lactose, cellobiose, raffinose, xylobiose, and sucrose. Among these saccharide residues, such-monosaccharide residues as of glucose, galactose, fucose, xylose, rhamnose, mannose, and fructose prove particularly advantageous. The hydrogen atom of the hydroxyl group in the saccharide residue represented by "X" may be substituted with a lower alkyl group, preferably a lower alkyl group of 1-8 carbon atoms, or a lower acyl group, preferably a lower acyl group of 1-10 carbon atoms. Further, n is an integer in the range of 0-6, preferably 1-4 and m is an integer in the range of 1-6, preferably 1-3. As preferred examples of the chromanol glycoside represented by the general formula (1), 2-(α-D-glucopyranosyl)methyl-2,5,7,8-tetramethylchroman-6-ol, 2-(β-D-galactopyranosyl)methyl-2,5,7,8-tetramethyl chroman-6-ol, 2-(β-L-fucopyranosyl)methyl-2,5,7,8-tetramethyl chroman-6-ol, 2-(α-L-rhamnopyranosyl)methyl-2,5,7,8-tetramethyl chroman-6-ol, 2-(β-D-xylopyranosyl)methyl-2,5, 7,8-tettramethyl chroman-6-ol, 2-(β-D-glucopyranosyl)methyl-2,5,7,8-tetramethyl chroman-6-ol, 2-(β-D-fructofuranosyl)methyl-2,5,7,8-tetramethyl chroman-6-ol, and 2-(α-D-mannopyranosyl)methyl-2,5,7,8-tetramethyl chroman-6-ol may be cited.

The chromanol glycoside which can be used in this invention may be produced by an enzymatic reaction (enzyme method) which comprises reacting a 2-substituted alcohol represented by the following general formula (2):

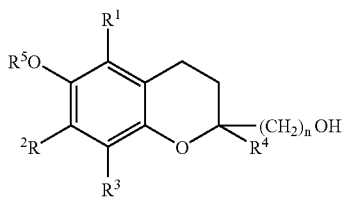

(2)

(wherein $R^1$, $R^2$, $R^3$, $R^4$, $R^5$ and n are as defined above) with an oligosaccharide in the presence of an enzyme capable of promoting the relevant saccharide transition thereby linking a specific hydroxyl group of the saccharide specifically to the hydroxyl group at the 2 position of the 2-substituted alcohol, in accordance with the methods disclosed in JP-A-7(1995)-118287, JP-A-9(1997)-249688, and JP-A-11(1999)-21291, for example.

The 2-substituted alcohol represented by the general formula (2) which is used as one of the raw materials in the reaction mentioned above (hereinafter referred to simply as "2-substituted alcohol") is a known substance and can be obtained by the method disclosed in JP-B-1(1989)-43755 and JP-B-1(1989)-49135, for example. The 2-substituted alcohol of the general formula (2) wherein $R^1$, $R^2$, $R^3$, and $R^4$ are a methyl group, $R^5$ is a hydrogen atom, and n is 1, for example, can be easily obtained as by heating and refluxing 6-hydroxy-2,5,7,8-tetramethyl chroman-2-carboxylic acid (commercial product "Trolox") having a structure resulting from substituting a carboxyl group for a phythyl group at the 2 position of the chroman ring of α-tocopherol in diethyl ether in the presence of lithium aluminum hydride.

The chromanol glycoside used in this invention can be otherwise produced by subjecting to condensation reaction the 2-substituted alcohol mentioned above having the hydroxyl group at the 6 position thereof protected with a protecting group and a saccharide derivative resulting from introducing a leaving group into the anomer position and protecting the other hydroxyl groups with a protecting group in accordance with the method disclosed in Japanese Patent Application No. 10-75599.

The chromanol glycoside according to this invention is a water-soluble vitamin E having lipophilic property. Unlike the conventional vitamin E derivatives which are insoluble in water or poorly soluble in water, the chromanol glycoside according to this invention, therefore, retains the lipophilic property even when it is used as dissolved in water and is consequently capable of permeating a cell membrane and entering a cell. Consequently, the chromanol glycoside can not only enhance effects of treatment with an anti-cancer agent but also repress effectively various side effects which are associated with the cancer chemotherapy. Further, the chromanol glycoside which is obtained by the reaction as mentioned above has significantly improved thermal stability and pH stability as compared with tocopherol, Trolox, or 2-substituted alcohol.

The ameliorating agent of this invention for the cancer chemotherapy can be used as a carcinostatic action-enhancing agent for enhancing the carcinostatic action of an anti-cancer agent in the cancer chemotherapy and as a side effect-repressing agent for repressing the side effects accompanied with the cancer chemotherapy.

The cancerous diseases in this invention include brain tumor, carcinoma of head and neck, gastric cancer, colon cancer, hepatic cancer, biliary tract cancer, pancreatic cancer, lung cancer, breast cancer, uterine cancer, ovarian cancer, prostatic cancer, bladder cancer, human bone and soft-tissue tumor, and leukemia, for example.

The term "cancer chemotherapy" as used in this invention refers to a therapy of cancer by the administration of an anti-cancer agent. As typical examples of the anti-cancer agent, cytotoxic anti-cancer agents such as an alkylating agent, an antineoplastic vegetable component-containing preparation, an antineoplastic antibiotic preparation, and a DNA chelating agent (a platinum compound) may be cited. As typical examples of the alkylating agent, chloroethyl amine type compounds such as cyclophosphamide, imidazol carboxamide, nitrogen mustard-N-oxide hydrochloride, melphalan, and ifosfamide, aziridine (ethyleneimine) type compounds such as carboquone and triethylene thiophosphoramide, sulfonic ester type compounds such as busulfan and isoprosulfan tosylate, epoxide type compounds such as mitobronitol, nitrosourea type compounds such as nimustine and ranimustine, estramustine sodium phosphate may be cited. As typical examples of the antineoplastic vegetable component-containing preparation, vinca alkaloid preparations such as vincristine sulfate, vinblastine sulfate, and vindesine sulfate, podophyllin preparations such as etoposide, and irinotecan hydrochloride may be cited. As typical examples of the antineoplastic antibiotic preparation, anthracyclines such as doxorubicin hydrochloride (adriamycin), idarubicin hydrochloride, daunorubicin hydrochloride, aclarubicin Hydrochloride, epirubicin hydrochloride, and purarubicin hycrochloroide, pleomycins such as pleomycin and peplomycin sulfate, mitomycins such as mitomycin C, actinomycins such as actinomycin D, zinostatinstimalamer, and polypeptides such as neocarzinostatin may be cited. As typical examples of the DNA chelating agent (platinum compound), cisplatin, carboplatin, and nedaplatin may be cited. As typical examples of other anti-cancer agents, sobuzoxane, tretinoin, pentostatin, L-asparaginase, flutamide, porphimer natrium, fadrozole hydrochloride, procarbazine hydrochloride, aceglatone, and mitoxantrone hydrochloride may be cited.

The side effects of the cancer therapy to which the ameliorating agent of this invention for cancer chemotherapy can apply include myelopathy like leukopenia, granulocytopenia, lymphopenia, thrombocytopenia, and erythropenia, hematopathy such as plasma fibrinogenopenia, digestive disorders such as nausea, vomiting, anorexia, heavy feeling of stomach, diarrhea, constipation, stomatitis, and esophagitis, pulmonary insufficiency such as chronic pneumonia and lung fibrosis, dermatopathy such as keratinization, pachymenia, chromatosis, epilation, rash, and nail alternation, nervous system disorder such as paresthesia, deep areflexia, neuroparalysis, auditory disorder, allolalia, disorientation, neurologic manifestation, cerebellar ataxia, somnolence, coma, vertigo, frequency of micturition, and frequency of defecation desire, endocrine disorder such as pituitary disorder, adrenal disorder, hyperglycemia, and hypoglycemia, genital disorder such as hyposexuality, oligospermia, gynecomastia menstrual disorder, cardiovascular disorder such as cardiomyopathy, arrhythmia, low blood pressure, tachycardia, and cardiac failure, hepatopathy, pancreatic disorder, nephropathy, bladder trouble, hyperuricemia, decrease of immunocompetence, and infection which are manifested in consequence of the cancer therapy mentioned above.

The ameliorating agent of this invention for the cancer chemotherapy may be administered either orally or parenterally prior to, during, or after the execution of the cancer chemotherapy by using the chromanol glycoside mentioned above either singly or as formulated with a pharmaceutically acceptable carrier or in the form of a composition having the chromanol glycoside dissolved or suspended in a pharmaceutically acceptable solvent.

When the ameliorating agent is used for the oral administration, the chromanol glycoside mentioned above may be used either singly or in the form of a solid preparation including tablet, powdered drug (powder), pill, or granules obtained by properly mixing the chromanol glycoside with a suitable additive such as, for example, an excipient like lactose, sucrose, mannitol, cornstarch, synthetic or natural rubber, and crystalline cellulose, a binder like starch, cellulose derivative, gum Arabic, gelatin, and polyvinyl pyrrolidone, a disintegrator like carboxy methylcellulose calcium, carboxymethylcellulose sodium, starch, corn starch, and sodium alginate, a lubricant like talc, magnesium stearate, and sodium stearate, a filler or diluent like calcium carbonate, sodium carbonate, calcium phosphate, and sodium phosphate. It may be used in a capsule form by using a hard or soft gelatin capsule. The solid preparation may be applied with an enteric coating by using a coating base such as hydroxypropyl methyl cellulose phthalate, hydroxypropyl methyl cellulose acetate succinate, cellulose acetate phthalate, and methacrylate copolymer. Further, the chromanol glycoside mentioned above may be used in a liquid preparation such as a syrup or an elixir by dissolving it in an ordinarily used inert diluent such as purified water and physiological saline and optionally adding the resultant solution with a wetting agent, an emulsifier, a dispersion auxiliary, a surfactant, a sweetener, a flavor, and a flavoring agent.

When the ameliorating agent for the cancer chemotherapy of this invention is to be used for the parenteral administration, the chromanol glycoside may be intravenously, subcutaneously, or intramuscularly injected in the form of a sterilized aqueous solution, non-aqueous solution, suspension, liposome, or emulsion having the chromanol glycoside combined properly with a purified water, or a suitable buffer solution such as phosphate buffer, physiological salt solution such as physiological saline, Ringer's solution, and Locke solution, ethanol, glycerin, and a commonly used surfactant, preferably in the form of a sterilized aqueous solution for injection. The liquid preparation used in this case properly has a physiological pH, preferably a pH in the range of 6-8. The ameliorating agent for the cancer chemotherapy of this invention may be percutaneously administered to a target site or the peripheral site thereof in the form of a liquid preparation such as lotion, suspension, or emulsion, a semi-solid preparation such as gel, cream, or ointment, or a solid preparation such as powder, dusting powder, or granule which is dissolved prior to actual application. It may be otherwise implanted in the form of a pellet or administered in the form of a suppository by using a suppository base. The form of preparation and the mode of administration can be properly selected by a physician in charge of the therapy.

Although the concentration of the chromanol glycoside to be contained in the ameliorating agent for the cancer chemotherapy of this invention may be varied with the mode of administration, the kind of disease, the seriousness of the disease, and the dosage, it is generally in the range of 0.1-100 mass %, preferably 1-90 mass %, based on the total mass of the raw materials. Particularly when the preparation of this invention is orally administered, the concentration is in the range of 1-100 mass %, preferably 5-90 mass %, based on the total mass of the raw materials. When it is parenterally administered, the concentration is in the range of 0.1-90 vol %, preferably 1-80 vol %, based on the total volume of the raw materials. In this case, if the concentration of the chromanol glycoside exceeds the upper limit of the range as specified above, the excess would disadvantageously fail to bring a proportionate addition to the repressing effects aimed at. Conversely, if the concentration is less than the lower limit of the range, the shortage would also disadvantageously result in preventing the repressing effect from being manifested fully satisfactorily.

The dosage of the ameliorating agent for the cancer chemotherapy of this invention may be varied depending on the age, body weight, and symptom of a patient, the mode and method of administration aimed at, the effects of therapy, and the duration of treatment, and should be accurately decided by the physician. Generally, the dose in the both cases for oral and parenteral administration is in the range of 0.01-2000 mg/kg of body weight as reduced to the dosage of chromanol glycoside.

The effects for enhancing the carcinostatic action and the effects for repressing side effects in the cancer chemotherapy using the ameliorating agent of this invention were confirmed by the following pharmacological test.

As the chromanol glucoside, 2-(α-D-glucopyranosyl)methyl-2,5,7,8-tetramethyl chroman-6-ol (TMG) represented by the following formula (3) which is produced by the method described in Example 1 of JP-A-7(1995)-118287 was used.

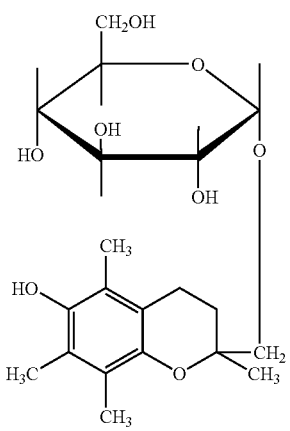

(3)

Confirmation Test for Effects of Enhancing Carcinostatic Action in Cancer Chemotherapy (1)

P388 leukemia cells ($6 \times 10^6$ cells) were administered intraperitoneally to female BDF mice of 8-9 weeks old (8 heads per group, body weight of 20-22 g). On the following day, a solution having prescribed amounts of cisplatin (CDDP) and TMG in 0.2 ml of physiological saline was intraperitoneally administered to the mice. The survival ratio of these mice was measured 60 days after the administration of CDDP and TMG. The results are shown in Table 1.

TABLE 1

| Dosage (mg/kg) | | Administration Date | Number surviving (Heads) | Survival ratio (%) |
|---|---|---|---|---|
| CDDP | TMG | | | |
| 0 | 0 | — | 0 | 0 |
| 0 | 0.01 | Every day from $1^{st}$-$9^{th}$ days | 0 | 0 |
| 0 | 0.1 | Every day from $1^{st}$-$9^{th}$ days | 0 | 0 |
| 0 | 1 | Every day from $1^{st}$-$9^{th}$ days | 0 | 0 |
| 2 | 0 | $1^{st}$, $3^{rd}$, $5^{th}$, and $7^{th}$ days | 6 | 75 |
| 2 | 0.01 | CDDP: $1^{st}$, $3^{rd}$, $5^{th}$, and $7^{th}$ days TMG: Every day from $1^{st}$-$9^{th}$ days | 8 | 100 |
| 2 | 0.1 | CDDP: $1^{st}$, $3^{rd}$, $5^{th}$, and $7^{th}$ days TMG: Every day from $1^{st}$-$9^{th}$ days | 8 | 100 |
| 2 | 1 | CDDP: $1^{st}$, $3^{rd}$, $5^{th}$, and $7^{th}$ days TMG: Every day from $1^{st}$-$9^{th}$ days | 8 | 100 |
| 4 | 0 | $1^{st}$, $5^{th}$, and $9^{th}$ days | 6 | 75 |
| 4 | 0.01 | CDDP: $1^{st}$, $5^{th}$, and $9^{th}$ days TMG: Every day from $1^{st}$-$9^{th}$ days | 7 | 87.5 |
| 4 | 0.1 | CDDP: $1^{st}$, $5^{th}$, and $9^{th}$ days TMG: Every day from $1^{st}$-$9^{th}$ days | 7 | 87.5 |
| 4 | 1 | CDDP: $1^{st}$, $5^{th}$, and $9^{th}$ days TMG: Every day from $1^{st}$-$9^{th}$ days | 8 | 100 |

The results of Table 1 indicate that TMG has action for enhancing the carcinostatic action of CDDP.

Confirmation Test for Effects of Enhancing Carcinostatic Action in Cancer Chemotherapy (2)

P388 leukemia cells ($6 \times 10^6$ cells) were administered intraperitoneally to female BDF mice of 8-9 weeks old (8 heads per group, body weight of 20-22 g). On the following day ($1^{st}$ day), cyclophosphamide (CPA) and TMG were administered at respective dose of 360 mg/kg and 0.01 mg/kg were intraperitoneally administered to the mice. Thereafter, CPA (360 mg/kg) was administered on the $3^{rd}$, $5^{th}$, and $7^{th}$ days and TMG (0.01 mg/kg) was administered every day from the $2^{nd}$ through $9^{th}$ days. The survival ratio of these mice was measured 60 days after the administration of CPA and TMG. The results are shown in Table 2.

TABLE 2

| Administration method | Number surviving (Heads) | Survival ratio (%) |
|---|---|---|
| No administration | 0 | 0 |
| CPA alone administered | 4 | 50 |
| TMG alone administered | 0 | 0 |
| CPA and TMG administered simultaneously | 6 | 75 |
| TMG administered 5 hours before administration of CPA | 8 | 100 |

The results of Table 2 indicate that TMG has action for enhancing the carcinostatic action of CPA.

Confirmation Test for Effects of Enhancing Carcinostatic Action in Cancer Chemotherapy (3)

P388 leukemia cells ($6 \times 10^6$ cells) were administered intraperitoneally to female BDF mice of 8-9 weeks old (8 heads per group, body weight of 20-22 g). On the following day ($1^{st}$ day), 16 mg/kg of adriamycin (ADM) and a prescribed amount TMG were intraperitoneally administered to the mice. Thereafter, ADM (16 mg/kg) was administered on the $3^{rd}$, $5^{th}$, and $7^{th}$ days and TMG (prescribed amount as mentioned above) was simultaneously administered every day on the $2^{nd}$-$7^{th}$ days. The survival ratio of these mice was measured 7 days after the administration of ADM and TMG. The results are shown in Table 3.

TABLE 3

| Dosage of TMG (mg/kg) | Number surviving (Heads) | Survival ratio (%) |
|---|---|---|
| 0 | 0 | 0 |
| 0.1 | 5 | 62.5 |
| 1.0 | 3 | 37.5 |
| 10 | 1 | 12.5 |
| 500 | 1 | 12.5 |

The results of Table 3 indicate that the carcinostatic action by ADM is significantly enhanced by the simultaneous administration with TMG. Further, it is indicated that the small dosage of TMG is more active than the large dosage of TMG.

Confirmation Test for Effects of Repressing Side Effects in Cancer Chemotherapy (1)

CDDP was intraperitoneally administered in a dosage of 16 mg/kg, a lethal dose, to 10 BDF mice of 8 weeks old (22-25 g). These mice formed Control Group. A group of mice to which CDDP was administered simultaneously with TMG in a dosage of 0.01 mg/kg formed Test Group 1 and a group of mice to which CDDP was administered simultaneously with TMG in a dosage of 1.0 mg/kg formed Test Group 2. The time course changes of survival ratio of the Control Group and Test Groups were measured. The results are shown in Table 4.

TABLE 4

| Days after administration | Survival ratio (%) | | |
|---|---|---|---|
| of CDDP | Control Group | Test Group 1 | Test Group 2 |
| 0 | 100 | 100 | 100 |
| 5 | 80 | 100 | 100 |
| 8 | 30 | 100 | 50 |
| 10 | 0 | 100 | 50 |

The results of Table 4 indicate that the groups involving additional administration of TMG show decreased toxicity of CDDP and a decreased death ratio of mice, as compared with the Control Group, and that Test Group 1 involving a smaller dosage manifests more outstanding effects.

Confirmation Test for Effects of Repressing Side Effects in Cancer Chemotherapy (2)

CDDP was intraperitoneally administered in a dosage of 2 mg/kg to 5 BDF mice of 8 weeks old once daily for 10 days. These mice formed Control Group. A group of mice to which CDDP was administered simultaneously with TMG in a dosage of 1 mg/kg once daily for 10 days formed Test Group.

The time course changes of the numbers of leukocytes in blood of the Control Group and Test Group were measured. The results are shown in Table 5.

TABLE 5

| Days after the | Number of leukocytes ($\times 10^4/\mu l$) | |
|---|---|---|
| start of test | Control Group | Test Group |
| 0 | 2.0 | 2.0 |
| 10 | 1.0 | 1.1 |
| 20 | 0.6 | 1.3 |
| 25 | 1.1 | 2.0 |

The results of Table 5 indicate that the group involving TMG administration shows very fast recovery of the number of leukocytes, as compared with the Control Group.

Confirmation Test for Effects of Repressing Side Effects in Cancer Chemotherapy (3)

CDDP was intraperitoneally administered in a dosage of 16 mg/kg, a lethal dose, to female BDF mice of 8-9 weeks old (8 heads per group, body weight of 20-22 g). After prescribed time therefrom, TMG was administered in a dosage of 0.01 mg/kg. After the elapse of 10 days, the mortalities of these mice were measured. The results are shown in Table 6.

TABLE 6

| Interval of TMG administration after CDDP administration (hr) | Survival ratio after 10 days (%) |
|---|---|
| 0 (Simultaneous administration) | 100 |
| 5 | 75 |
| 10 | 0 |

The results of Table 6 indicate that the detoxication effects are improved as the interval between the administration of CDDP and the administration of TMG decreases, and that the simultaneous administration with CDDP was most effective.

Confirmation Test for Effects of Repressing Side Effects in Cancer Chemotherapy (4)

P388 leukemia cells ($6 \times 10^6$ cells) were administered intraperitoneally to female BDF mice of 8-9 weeks old (8 heads per group, body weight of 20-22 g). On the following day, ADM was administered in a dosage of 16 mg/kg once daily for 9 days. The mice formed Control Group. A group of mice to which TMG was administered simultaneously with ADM in a dosage of 0.1 mg/kg once daily for 9 days formed Test Group.

The time-course changes of the body weight of the Control Group and Test Group were measured. The results are shown in Table 7.

TABLE 7

| Days after start | Decrease of body weight (g) | |
|---|---|---|
| of the test | Control Group | Test Group |
| 1 | 1.5 | 2.0 |
| 3 | 3.3 | 3.1 |
| 5 | 5.7 | 4.1 |
| 7 | 6.5 | 3.0 |
| 9 | — | 1.5 |

The results of Table 7 indicate that the combined use of TMG in a small dosage represses the decrease of body weight of mice due to the administration of ADM and promotes recovery from the side effect.

Test of Acute Toxicity

The ameliorating agent for cancer chemotherapy of this invention was tested for acute toxicity to confirm the safety thereof. To groups each of 3 ICR mice of 4-5 weeks, the same TMG as mentioned above was suspended as the chromanol glycoside in a 5% gum arabic solution. The resultant suspension was orally administered in a dosage of 500 mg/kg as reduced to TMG. For one week, the mice were kept under observation. In this case, to the mice of the Control Group, 0.3 ml of a 5% gum arabic solution was orally administered. No dead mice were found in either of the groups used in the present test.

PREPARATION EXAMPLE 1

A dusting powder was obtained by mixing 100 g of TMG, 800 g of lactose, and 100 g of corn starch with a blender.

PREPARATION EXAMPLE 2

A granule was obtained by mixing 100 g of TMG, 450 g of lactose, and 100 g of hydroxypropyl cellulose of a low degree of substitution, adding 350 g of an aqueous 10% hydroxypropyl cellulose solution to the resultant mixture, kneading them, granulating the resultant blend with an extruder, and drying the resultant pellets.

PREPARATION EXAMPLE 3

A tablet was obtained by mixing 100 g of TMG, 550 g of lactose, 215 g of corn starch, 130 g of crystalline cellulose, and 5 g of magnesium stearate with a blender, and molding the resultant mixture in the shape of tablets with a tabletting device.

PREPARATION EXAMPLE 4

A capsule was obtained by mixing 100 g of TMG, 110 g of lactose, 58 g of corn starch, and 2 g of magnesium stearate with a V-shaped mixer, and filling No. 3 capsules each with 180 mg of the resultant mixture.

FORMULATION EXAMPLE 5

An injection was obtained by dissolving 200 mg of TMG and 100 mg of glucose in 2 ml of purified water, filtering the resultant solution, dispensing the filtrate in 2-ml ampoules, sealing the filled ampoules, and sterilizing the completed ampoules.

FORMULATION EXAMPLE 6

A lotion was obtained by mixing 1 g of TMG, 3 g of ethanol, 0.2 g of hydroxyethyl cellulose, and 0.1 g of methyl paraoxybenzoate, and dissolving the resultant mixture in 100 ml of purified water.

INDUSTRIAL APPLICABILITY

The ameliorating agent for cancer chemotherapy of this invention has a water-soluble chromanol glycoside as an active ingredient thereof, as mentioned above. The use of this ameliorating agent in cancer chemotherapy results in enhancing the carcinostatic action in the cancer chemotherapy and repressing truly effectively serious side effects manifested in consequence of the cancer chemotherapy as well. It, therefore, enables the cancer chemotherapy to be continued while keeping the dosage of the anti-cancer agent at a necessary level. Accordingly, the ameliorating agent of this invention is capable of deriving the efficacy of cancer chemotherapy to the fullest possible extent and relieving a patent of his physical burden at the same time.

The invention claimed is:

1. A composition for cancer chemotherapy, which comprises an effective amount of an anti-cancer agent and an effective amount of a chromanol glycoside that is 2-($\alpha$-D-glucopyranosyl)methyl-2,5,7,8-tetramethyl chroman-6-ol, wherein said anti-cancer agent is doxorubicin hydrochloride and wherein said chromanol glycoside is an agent for repressing a side effect of said anti-cancer agent wherein said side effect is decrease in body weight.

2. The composition according to claim 1, wherein said cancer is leukemia.

* * * * *